United States Patent [19]
Studer et al.

[11] Patent Number: 6,096,924
[45] Date of Patent: Aug. 1, 2000

[54] PROCESS FOR THE CATALYTIC HYDROGENERATION OF AROMATIC NITRO COMPOUNDS

[75] Inventors: Martin Studer, Basel; Peter Baumeister, Flüh, both of Switzerland

[73] Assignee: Novartis AG, Basel, Switzerland

[21] Appl. No.: 08/952,459

[22] PCT Filed: May 7, 1996

[86] PCT No.: PCT/EP96/01889

§ 371 Date: Nov. 13, 1997

§ 102(e) Date: Nov. 13, 1997

[87] PCT Pub. No.: WO96/36597

PCT Pub. Date: Nov. 21, 1996

[30] Foreign Application Priority Data

May 19, 1995 [CH] Switzerland ............................ 1495/95

[51] Int. Cl.[7] ...................... C07C 303/40; C07C 231/12; C07C 209/36
[52] U.S. Cl. ........................... 564/86; 564/168; 564/417; 564/418; 564/421; 564/422; 564/423; 562/47; 562/60
[58] Field of Search ............................... 564/86, 417, 418, 564/421, 422, 423, 168; 562/47, 60

[56] References Cited

U.S. PATENT DOCUMENTS

| | | | |
|---|---|---|---|
| 3,666,813 | 5/1972 | Hindin et al. | 260/580 |
| 3,944,615 | 3/1976 | Iqabal | 260/580 |
| 4,020,107 | 4/1977 | Kosak . | |
| 4,212,824 | 7/1980 | Seagraves | 260/580 |
| 5,856,578 | 1/1999 | Siegrist et al. | 564/423 |

FOREIGN PATENT DOCUMENTS

| | | |
|---|---|---|
| 0 002 308 | 6/1979 | European Pat. Off. . |
| 2 042 368 | 4/1971 | Germany . |
| 2 214 056 | 10/1973 | Germany . |
| 25 19 838 | 11/1976 | Germany . |
| 2519838 | 11/1976 | Germany . |
| 28 49 002 | 5/1980 | Germany . |
| 799871 | 8/1958 | United Kingdom . |
| 95 32941 | 12/1995 | WIPO . |
| 95 32952 | 12/1995 | WIPO . |

OTHER PUBLICATIONS

F. Stoessel, J. Loss Prev. Process Ind., 1993, vol. 6, No. 2, pp. 79–85.
J.A. Miller, Cancer Research (1970) 30, pp. 559–576.
Derwent Abstract, 86–046753 (1986) of SU 285689A.
Chem. Abstr., vol. 76:104258a (1972) of Bizhanov, et al.
Tong et al., AICHE Loss Prev. 1997, (11), pp. 71–75.
J.R. Kosak, Catalysis in Organic Synthesis, vol. 18, 1988, pp. 135–147.
J. R. Kosak, Catalysis in Organic Synthesis, 1980, pp. 107–117.
Miller, J.A., "Carcinogenesis by Chemicals: An Overview— G. H. A. Clowes Memorial Lecture," Cancer Research, vol. 30, 1970, pp. 559–576.
Stoessel, F., "Experimental study of thermal hazards during the hydrogenation of aromatic nitro compounds," J. Loss Prev. Process Ind., vol. 6, No. 2, 1993, pp. 79–85.
Tong et al., "3–4–Dichloroaniline Autoclave Incident," AICHE Loss Prev., vol. 11, 1977, pp. 71–75.
Kosak, J.R., "Hydrogeneration of Nitroarenes—The Hydroxylamine Intermediate," Catalysis of Organic Reactions, Dec. 1988, pp. 135–147.
Kosak, J.R., Catalysis in Organic Synthesis, 1980, pp. 107–117.
Marino, J.P. et al., Synthetic Communications, vol. 24, No. 6, 1994, pp. 839–848.
Rylander, P.N., Hydrogenation Methods, Academic Press, London, 1985, pp. 326–329.
Rylander, P.N., Catalytic Hydrogenation in Organic Synthesis, Academic Press, London, 1979, p. 140.
Rylander, P.N., Hydrogenation Methods, Academic Press, London, 1985, p. 77.
Freifelder, M., Practical Catalytic Hydrogenation, Wiley, New York, 1971, p. 256.
Freifelder, M., Practical Catalytic Hydrogenation, Wiley, New York, 1971, pp. 306–306.
Derwent Abstract, 86–046753 (1986) of SU 285689A.
Chem. Abstr. vol. 76:104258a (1972) of Bizhanov, et al.

*Primary Examiner*—Peter O'Sullivan
*Attorney, Agent, or Firm*—Wenderoth, Lind & Ponack, L.L.P.

[57] ABSTRACT

One object of the invention is a process for the catalytic hydrogenation of aromatic nitro compounds in solution or in melt in the presence of hydrogen and at least one noble metal catalyst, nickel catalyst or cobalt catalyst, in which process a catalytic amount of at least one vanadium compound is present, wherein the vanadium has the oxidation state 0, II, IV or V. It has been found that in the catalytic hydrogenation of aromatic nitro compounds the accumulation of hydroxylamines can be almost completely prevented by the addition of catalytic amounts of vanadium compounds, which usually results in concentrations of <1% hydroxylamine. The resulting hydrogenated products are whiter (purer) than those obtained without the addition of the vanadium compound because almost no azo or azoxy compounds are obtained. The hydrogenation, in particular the final phase, proceeds faster than without said addition. Accordingly, substantial advantages with respect to quality constancy and economy are obtained.

23 Claims, No Drawings

PROCESS FOR THE CATALYTIC HYDROGENERATION OF AROMATIC NITRO COMPOUNDS

This application is a 371 of PCT/EP96/01889.

The present invention relates to a process for the hydrogenation of unsubstituted or substituted aromatic nitro compounds with hydrogen in the presence of known hydrogenation catalysts, typically Rh, Ru, Pt, Pd, Ir, Ni or Co, at which hydrogenation catalytic amounts of at least one vanadium compound must be present. The invention also relates to the use of vanadium compounds in the catalytic hydrogenation of aromatic nitro compounds with hydrogen in the presence of known hydrogenation catalysts.

The catalytic hydrogenation of aromatic nitro compounds is a reaction which is industrially important, for example for the preparation of intermediates for agrochemicals, dyes and fluorescent whitening agents. For the preparation of stilbene fluorescent whitening agents, for example, 4,4'-dinitrostilbene-2,2'-disulfonic acid has to be reduced to 4,4'-diaminostilbene-2,2'-disulfonic acid, which may be achieved by classical reduction processes or by catalytic hydrogenation. The preparation of azo dyes requires large amounts of diazonium salts which in turn are prepared from the corresponding amines.

Catalytic hydrogenations of aromatic nitro compounds to the corresponding aromatic amines proceed via several intermediary stages. Important among these are the corresponding nitroso compounds and, in particular, the hydroxylamine intermediate, as is described, inter alia, by M. Freifelder in Handbook of Practical Catalytic Hydrogenation, Verlag Wiley-Interscience, New York, 1971.

This hydroxylamine intermediate poses a special problem in practice, because under specific conditions it can accumulate in large amounts in reaction solutions. This applies in particular to aromatic nitro compounds, the hydrogenation of which results in relatively stable arylhydroxylamines. This is particularly critical when the hydrogenation is carried out in a slurry batch reactor. In the extreme case, several tons of arylhydroxylamine can thus be formed.

Arylhydroxylamines are in many respects problematical. For one thing it is known that such compounds are often thermally instable and can disproportionate during heating with or without $H_2$ with strong emission of heat. The liberated heat can trigger further decomposition reactions which can then result in incidents with heavy explosions. W. R. Tong et al, AICHE Loss Prev. 1977, (11), 71–75 describe such an incident during the reduction of 3,4-dichloronitrobenzene to 3,4-dichloroaniline.

This instability makes a thorough and elaborate thermal examination of hydrogenation mixtures imperative. In particular, the thermal behaviour of the possible hydroxylamine intermediates must be thoroughly examined. F. Stoessel, J. Loss Prev. Process Ind., 1993, Vol 6, No 2, 79–85 describes this procedure, using the hydrogenation of nitrobenzene to aniline as an example.

Arylhydroxylamines are also known as strong carcinogens and therefore constitute a high hazard potential in the case of interrupted or incomplete hydrogenation (J. A. Miller, Cancer Res. 3 (1970),559).

The preparation of a pure amine constitutes a third complex of problems. If, during the hydrogenation or at the end of the reaction, significant amounts of arylhydroxylamine are present, then this may lead to condensations with formation of unwanted and dyed azo or azoxy products. Since the amount of arylhydroxylamine can change from batch to batch, the resulting product quality differs in purity and aspect.

The problems indicated above are further aggravated by the fact that the resulting concentrations or even the maximum possible concentrations of this hydroxylamine intermediate cannot be predicted even in processes which are known and well-studied. The presence of impurities in the trace range can trigger the spontaneous accumulation of hydroxylamine intermediates in unpredictable manner. In, for example, Catalysis of Organic Reactions, Vol 18, (1988), 135, J. R. Kosak relates that the simple addition of 1% of $NaNO_3$ increases the accumulation during the hydrogenation of 3,4-dichloronitrobenzene from the initial <5% to about 30%.

To solve these problems, different processes have been proposed in the prior art. DE-OS-25 19 838. for example, discloses a continuous process for the catalytic hydrogenation of nitro compounds to the corresponding amino compounds in which the catalyst particles of 0.5 to 3 mm are arranged in a fixed bed and the nitro compounds are carried in the trickling phase. The catalyst is preferably applied to a carrier, typically aluminium oxide or silicic acid.

A similar continuous process is disclosed in DE-OS-22 14 056. In this process the nitro compound is also lead over the fixed catalyst. Said catalyst consists of aluminium spinel as carrier on which palladium and vanadium or vanadium compounds are fixed.

DE-OS 28 49 002 discloses a process for the hydrogenation of nitrobenzene in the vapour phase in a continuous process in the presence of a multicomponent carrier catalyst comprising 1–20 g of a noble metal and 1–20 g of, for example, vanadium or of a vanadium compound per liter of carrier material.

For the reduction of aromatic nitro compounds in a batch reaction, U.S. Pat. No. 4,212,824 proposes the use of an iron-modified platinum catalyst for the hydrogenation. In practice, however, this iron-modified platinum catalyst cannot entirely satisfy. In many cases the formation of hydroxylamine is, on the one hand, not completely prevented but, on the other hand, the rate of hydrogenation can be markedly slowed down.

These proposals of the prior art all have in common that the actual catalyst is modified such, and its activity is thereby adjusted such, that no great amount of accumulation of hydroxylamine can occur, in particular in the continuous process. In the continuous processes this is in any case substantially less critical than in batch processes because continuous processes have a substantially lower amount of educt and product in the actual reaction volume. On the other hand, continuous processes are only economical in the case of products with large tonnages so that there is still a desire for an easily controllable reaction, essentially without hydroxylamine accumulation. This is particularly important with respect to batch reactions. Furthermore, the preparation of the above-described fixed bed catalysts involves a great amount of expenditure and is complicated, which also reduces the economy of such operational processes.

Surprisingly, it has now been found that in the catalytic hydrogenation of aromatic nitro compounds the accumulation of hydroxylamines can be almost completely prevented by the addition of catalytic amounts of vanadium compounds, which usually results in concentrations of <1% of hydroxylamine.

This result can be achieved with any commercially obtainable hydrogenation catalyst. A special pretreatment or modification of the catalyst, as known from the prior art, is not necessary.

The resulting hydrogenated products are whiter (purer) than those obtained without the addition of the vanadium compound because almost no azo or azoxy compounds are obtained. The hydrogenation, in particular the final phase, proceeds faster than without said addition. Accordingly, substantial advantages result with respect to quality constancy and economy.

Compared to the prior art, this invention has the substantial advantage that catalytic amounts of a vanadium compound can be easily dissolved or dispersed in the reaction medium, affording excellent hydrogenation results.

One object of the invention is a process for the catalytic hydrogenation of aromatic nitro compounds in solution or in melt in the presence of hydrogen and at least one noble metal catalyst, nickel catalyst or cobalt catalyst, in which process a catalytic amount of at least one vanadium compound is present, wherein the vanadium has the oxidation state 0, II, III, IV or V.

A preferred process is that wherein the vanadium compound is dissolved or dispersed in catalytic amounts in the reaction medium; preferably it is dissolved.

Another likewise preferred process is obtained when the vanadium compound is mixed with the catalyst or is applied thereto.

It is also preferred to apply the vanadium compound first to a suitable carrier and then to disperse it in this form in the reaction medium.

Suitable carrier materials are, for example, all those used for the preparation of commercial hydrogenation catalysts in powdered form, such as those indicated below.

Application to the catalyst or to the carrier material is carried out in simple manner, typically by dissolving the vanadium compounds, suspending the catalyst or the carrier material in the solution and subsequent filtration.

If the vanadium compounds are not soluble in the reaction medium, then they can also be mixed in disperse slurried form with the slurried catalyst and filtered together.

Suitable vanadium compounds of the oxidation state 0, II, III, IV or V are elemental vanadium as well as purely inorganic compounds, but organic complexes with, for example, oxalate or acetylacetonate are also possible.

Preferred vanadium compounds are $V_2O_5$ or those which constitute a purely inorganic salt, oxo salt or the hydrate of a purely inorganic salt or oxo salt. Typical examples are $VOCl_3$, $VCl_6^-$, $[VO(SCN)_4]^{2-}$, $VOSO_4$, $NH_4VO_3$, $VCl_3$, $VCl_2$ or the corresponding halides with F or Br. The compounds are obtained in aqueous solution in different hydrate forms, depending on the pH (F. A. Cotton, G. Wilkinson, Anorganische Chemie, Verlag Chemie Weinheim 1968, 2nd edition, pages 757–766). Particularly preferred vanadates or hydrates of vanadates are those of oxidation state V. The ammonium, lithium, sodium or potassium vanadates, or a hydrate of these vanadates, are very particularly preferred.

It is preferred to use the vanadium compound in an amount of 1–2000 ppm, particularly preferably in an amount of 5–500 ppm, based on the aromatic nitro compound to be hydrogenated.

The weight ratio of vanadium compound to catalyst is preferably from 1:1 to 1:10 000, particularly preferably from 1:10 to 1:1000 and, very particularly preferably, from 1:50 to 1:750.

The aromatic nitro compounds can be substituted by any groups that are inert during the hydrogenation or also by further groups which can be hydrogenated, e.g. olefinic groups. A concomitant hydrogenation of all groups may sometimes be desired.

The aromatic nitro compounds can comprise one or more than one nitro group.

Some examples of aromatic nitro compounds are aromatic hydrocarbons, typically benzenes, polycyclic hydrocarbons (also partially hydrogenated ones such as tetralin), biphenyls, cyclopentadienyl anion and cycloheptatrienyl anion, heteroaromatics, typically pyridines, pyrroles, azoles, diazines, triazines, triazoles, furans, thiophenes and oxazoles, condensed aromates, typically naphthalene, anthracene, indoles, quinolines, isoquinolines, carbazoles, purines, phtalazines, benzotriazoles, benzofurans, cinnolines, quinazoles, acridines and benzothiophenes. Said compounds will also be understood to include conjugated aromatic systems such as stilbenes or cyanines under the condition that the nitro group is bonded to the aromatic part of the conjugated aromatic system.

A preferred subgroup is formed by aromatic nitro compounds, wherein the aromatic radical is substituted by electrophilic groups.

Electrophilic groups are typically halogen, sulfonic acid radicals and their derivatives, carboxylic acid radicals or their derivatives, such as ester, acid chloride or nitriles.

Halogen is fluoro, chloro, bromo or iodo. Fluoro, chloro or bromo are preferred.

Preferred electrophilic groups are halogen, —$SO_3M$, —COX, wherein M is hydrogen or an alkali metal and X is halogen or O—$C_1$–$C_{12}$alkyl.

$C_1$–$C_{12}$Alkyl can be methyl, ethyl, isopropyl, n-propyl, n-butyl, isobutyl, sec-butyl, tert-butyl as well as the different isomeric pentyl, hexyl, heptyl, octyl, nonyl, decyl, undecyl and dodecyl radicals.

Very particularly preferred is the aromatic nitro compound 4,4'-dinitrostilbene-2,2'-disulfonic acid or a compound of formula II, III or IV

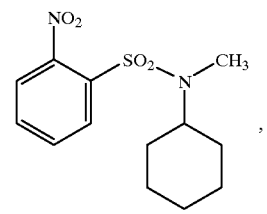

(II)

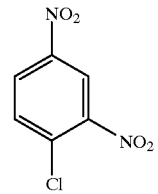

(III)

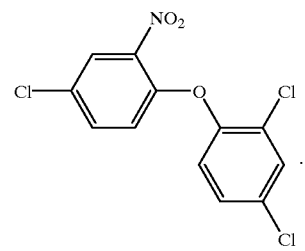

(IV)

In principle, the process is suitable for all reductions of aromatic nitro groups to aromatic amines carried out on a large industrial scale. Typical examples are intermediates for agrochemicals, fluorescent whitening agents and dyes.

The process of this invention is particularly suitable for the preparation of aromatic amino compounds, such as those disclosed, inter alia, in EP-A-42357, which are used for the preparation of diazonium salts in the synthesis of azo dyes.

The reaction can be carried out in solution in a suitable solvent which is inert during the reaction, but can also be carried out in the melt of the educt.

Suitable solvents are typically water, alcohols, such as methanol, ethanol, n-propanol, isopropanol, n-butanol, the isomeric butanols and cyclohexanol, ethers, esters and ketones, typically diethyl ether, methyl-tert-butyl ether, tetrahydrofuran, dioxane, dimethoxyethane, ethyl acetate, butyl acetate, butyrolactone, acetone, methyl ethyl ketone, methyl-isobutyl ketone or cyclohexanone, carboxylic acids, typically acetic acid and propionic acid, dipolar/aprotic solvents, such as dimethyl formamide, N-methylpyrrolidone, dimethylacetamide, sulfolane, dimethyl sulfoxide or acetonitrile, apolar solvents, typically toluene or xylene, chlorinated aromatic hydrocarbons, typically methylene chloride, $C_3$–$C_7$alkane or cyclohexane.

These solvents can be used in pure form or in the form of mixtures.

The noble metal catalyst can contain rhodium, ruthenium, iridium, palladium or platinum as noble metals. Nickel catalysts or cobalt catalysts are also suitable. The nickel catalyst can be, for example, Raney nickel.

In a preferred embodiment of this invention, the noble metal catalyst is platinum, palladium, iridium, rhodium or ruthenium in metallic or oxidised form which is applied to a carrier. The metallic form is particularly preferred.

Platinum or palladium are very particularly preferred.

Particularly suitable carriers are activated carbon, silicic acid, silica gel, aluminium oxide, calcium carbonate, calcium phosphate, calcium sulfate, barium sulfate, titanium oxide, magnesium oxide, iron oxide, lead oxide, lead sulfate or lead carbonate. Activated carbon, silica gel, aluminium oxide or calcium carbonate are very particularly suitable.

It is preferred to use the noble metal catalyst in an amount of 0.1 to 5% by weight, based on the aromatic nitro compound.

The process is preferably carried out at a pressure of $1 \cdot 10^5$–$2 \cdot 10^7$ pascal.

The process is preferably carried out in the temperature range of 0–300° C., particularly preferably of 20–200° C.

The process can be carried out as a batch or continuous process. The batch process is preferred.

The invention also relates to the use of vanadium compounds according to claim 1 for the catalytic hydrogenation of aromatic nitro compounds in solution or in melt in the presence of hydrogen and at least one noble metal catalyst, nickel catalyst or cobalt catalyst.

The following Examples illustrate the invention in more detail. The reaction rates were determined by NMR spectroscopy and the percentages are by weight.

EXAMPLE 1

A 300 ml autoclave equipped with a sparger is charged, under pressure, with 77 g of the compound of formula II

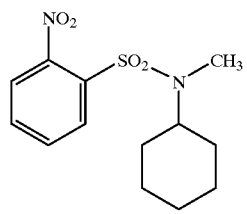

(II)

110.5 ml of tetrahydrofuran absolute (Merck p.a.), 530 mg of 5% Pd/C (Johnson Matthey 87L) and 19.4 mg of $NH_4VO_3$ are then added. The air in the autoclave is replaced with $N_2$ and the reaction mixture is heated to 120° C. At 120° C., $N_2$ is replaced with $H_2$ (20 bar) and the sparger is started.

After a reaction time of 120 minutes, 100% of the amino compound are obtained and 0% of hydroxylamine. Throughout the reaction no formation of hydroxylamine can be detected.

Comparison Example 1a

Example 1 is repeated, but without the addition of $NH_4VO_3$.

After a reaction time of 150 minutes, 84% of the amino compound and 16% of hydroxylamine are obtained. The maximum concentration of hydroxylamine during the reaction is 41%.

EXAMPLE 2

Preparation of Aniline-2-sulfonic Acid-(N-cyclohexyl-N-methyl)amide

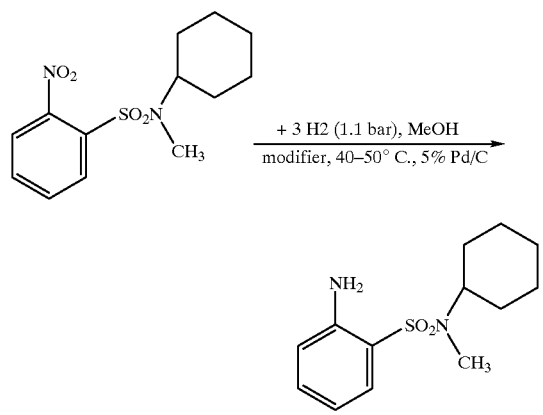

A 500 ml shaker flask is charged with 13.0 g of nitrobenzene-2-sulfonic acid-(N-cyclohexyl-N-methyl)amide, 130 g of methanol, 0.895 g of 5% Pd/C and vanadium modifier (Table 1). The shaker flask is evacuated 3 times and flushed with hydrogen. The temperature is elevated to 40–50° C. and the reaction is started (1.1 bar of hydrogen). During the reaction, 4–5 samples are taken to check the reaction. These samples as well as the reaction product are analysed with 1H-NMR. The results listed in Table 1 are obtained.

TABLE 1

| Exp. | Modifier | Amount | $t_R$* | [Amine] acc. to $t_R$ | [Hydroxylamine] acc. to $t_R$ | Hydroxylamine max |
|---|---|---|---|---|---|---|
| 2a | — | — | 275 min | 90% | 10% | 33% |
| 2b | $NH_4VO_3$ | 1.9 mg | 110 min | 100% | 0% | 10% |
| 2c | $VOSO_4 \cdot 5H_2O$ | 4.1 mg | 77 min | 100% | 0% | 14% |
| 2d | 3% $V_2O_5/SiO_2$ | 30 mg | 89 min | 95% | 5% | 22% |
| 2e | $NH_4VO_3/C$** | 2.5 mg | 110 min | 100% | 0% | 8% |

*$t_R$ = reaction time
**$NH_4VO_3$ deposited on activated carbon

EXAMPLE 3

Preparation of 3-Amino-4-chloro-acetanilide

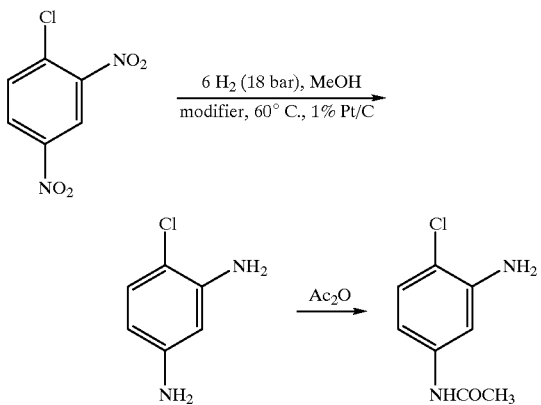

Example 3a. A hydrogenation reactor is charged with 15 parts of sodium acetate, 60 parts of NaHCO$_3$, 1320 parts of MeOH and 1015 parts of 1-chloro-2,4-dinitrochlorobenzene under nitrogen at 50° C. and then 11 parts of 1% Pt/C, 0.15 parts of NH$_4$VO$_3$ and 66 parts of water are added. The hydrogenation is carried out at 60° C. and 18 bar. The product is isolated as 3-amino-4-chloroacetanilide (785 parts, 85% of theory).

Example 3b. A 0.3 l Hastalloy B autoclave is charged with 40.8 g of 1-chloro-2,4-dinitrochlorobenzene, 120 ml of methanol and 0.21 g of 5% Pt/C catalyst. The mixture is flushed with nitrogen and then hydrogenated with hydrogen at 60° C. and 10 bar. The selectivity with respect to dehalogenation is 66%.

EXAMPLE 4

Preparation of 2,4,4'-Trichloro-2'-aminodiphenyl Ether (TADE)

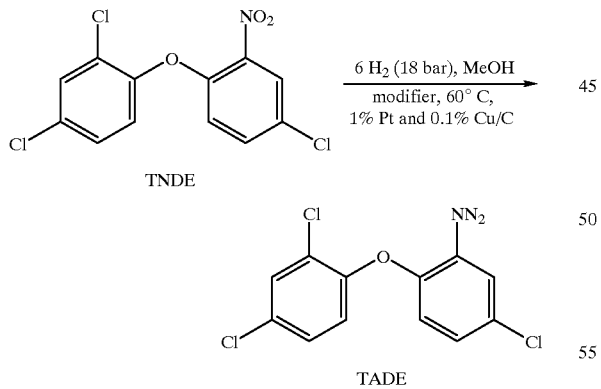

A 2 l steel autoclave is charged with 330 g of 2,4,4'-trichloro-2'-nitrodiphenyl ether, 330 g of MeOH, 2.8 g of 1% Pt+0.1% Cu/C. The autoclave is closed and flushed with nitrogen. The hydrogenation is carried out at hydrogen pressure of 12 bar and at 60° C. After consumption of specific percentages of the calculated amount of hydrogen, the hydrogenation is interrupted and a sample is taken from the reaction mixture. The sample is heated in the DSC temperature-programmed at 4° C./min and the liberated energy of decomposition is measured. The disproportionation of the arylhydroxylamine is given a thermal signal which is already visible at <100° C. The decomposition of the nitro compound still present in the reaction mixture (rm) starts at >200° C. The results are listed in Table 2.

TABLE 2

| Exp. | Modifier | H2 Consumption [% of theory] | Energy of decomposition <100° C. [kJ/kg rm] | Energy of decomposition >200° C. [kJ/kg rm] |
|---|---|---|---|---|
| 4a | none | 75% | −127 | −1423 |
| 4b | 110 mg NH$_4$VO$_3$ | 60% | 0 | −1273 |

The risk that a spontaneous decomposition of the accumulated arylhydroxylamine will trigger the decomposition of the nitro compound can be remarkably reduced.

EXAMPLE 5

Preparation of Sodium 4,4'-Diaminostilbene-2,2'-disulfonate (DAS)

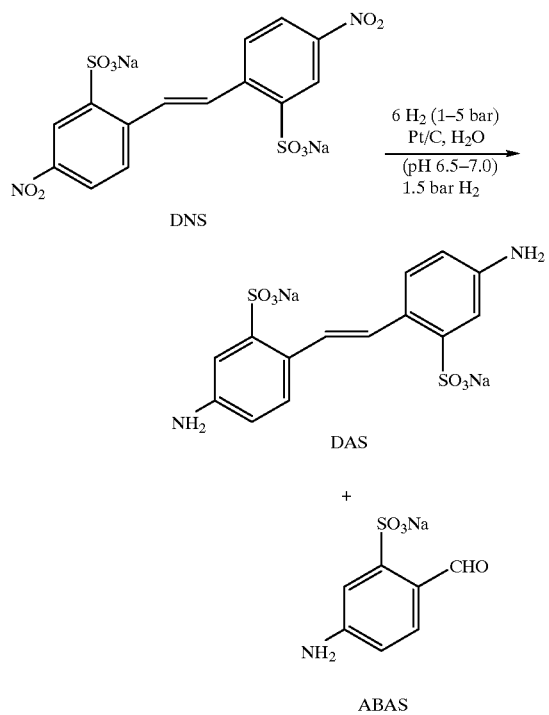

A 300 ml steel autoclave is charged with 48 g of sodium 4,4'-dinitrostilbene-2,2'-disulfonate, 174 g of water, 0.15 ml of 0.5 M H$_2$SO$_4$, 1.4 g of activated carbon, 64 mg of 5% Pt/C and 12 mg of NH$_4$VO$_3$. The autoclave is closed and flushed with nitrogen. The hydrogenation is carried out at 70° C. with the controlled addition of hydrogen of 2.5 Nl/h (max. 4–5 bar hydrogen). After the hydrogenation is terminated, the autoclave is rendered inert, the catalyst is filtered off and the reaction mixture is analysed with HPLC. The results are listed in Table 3.

TABLE 3

| Exp. | NH₄VO₃ | Carbon | Content DAS | ABAS | Azo and azoxy compounds | Unknown |
|---|---|---|---|---|---|---|
| 5a | — | — | 94.9% | 3.5% | 0.3% | 1.3% |
| 5b | — | 1.44 g | 93.8% | 4.1% | 0.4% | 1.7% |
| 5c | 12 mg | — | 94.7% | 3.9% | 0.3% | 1.1% |
| 5d | 12 mg | 1.44 g | 98.3% | 1.0% | 0.4% | 0.3% |

The selectivity of the hydrogenation of DNS is highly dependent on the availability of the hydrogen on the surface of the catalyst. The hydrogenation is therefore preferably carried out under high pressure in well-gassifying reactors. In accordance with the described process it is possible to carry out the hydrogenation at a low $H_2$ partial pressure and still obtain good product quality. The hydrogenated product is an intermediate for the preparation of fluorescent whitening agents. The rate of reaction and therefore also the heat flow resulting from the hydrogenation can thus be controlled via the $H_2$ dosage.

What is claimed is:

1. A process for reducing aromatic nitro compounds in solution or in melt which comprises catalytically hydrogenating said compounds in the presence of:
   a) hydrogen;
   b) at least one noble metal catalyst, nickel catalyst, or cobalt catalyst deposited on a carrier and in powder form; and
   c) 1–2000 ppm (based on said aromatic nitro compounds) of at least one vanadium compound of oxidation state 0, II, III, IV, or V, wherein said vanadium compound is dissolved or dispersed in said solution or melt.

2. A process of claim 1 wherein the vanadium compound is dissolved.

3. A process of claim 1 wherein the vanadium compound is dispersed.

4. A process of claim 3, wherein the vanadium compound is mixed with a carrier material or is applied thereto.

5. A process of claim 1, wherein the vanadium compound is $V_2O_5$ or a purely inorganic salt, oxo salt or the hydrate of a purely inorganic salt or oxo salt.

6. A process of claim 1, wherein the vanadium compound is a vanadate or the hydrate of a vanadate of oxidation state V.

7. A process of claim 1, wherein the vanadium compound is an ammonium, lithium, sodium or potassium vanadate, or a hydrate of these salts.

8. A process of claim 1, which comprises using the vanadium compound in an amount of 5–500 ppm, based on the aromatic nitro compound to be hydrogenated.

9. A process of claim 1, wherein the weight ratio of vanadium compound to catalyst is from 1:1 to 1:10 000.

10. A process of claim 9, wherein the weight ratio of vanadium compound to catalyst is from 1:10 to 1:1000.

11. A process of claim 10, wherein the weight ratio of vanadium compound to catalyst is from 1:50 to 1:750.

12. A process of claim 1, wherein the catalyst contains as noble metal rhodium, ruthenium, iridium, palladium, platinum or, as base metal, nickel or cobalt.

13. A process of claim 12, which comprises using a noble metal catalyst wherein the rhodium, ruthenium, iridium, platinum or palladium is applied in metallic or oxidised form on a carrier.

14. A process of claim 13, wherein the carrier is activated carbon, silicic acid, silica gel, aluminium oxide, calcium carbonate, calcium phosphate, calcium sulfate, barium sulfate, titanium oxide, magnesium oxide, iron oxide, lead oxide, lead sulfate or lead carbonate.

15. A process of claim 14, wherein the carrier is activated carbon, silica gel, aluminium oxide or calcium carbonate.

16. A process of claim 15, wherein the catalyst comprises platinum or palladium.

17. A process of claim 1, which comprises using the noble metal catalyst in an amount of 0.1 to 5% by weight, based on the aromatic nitro compound.

18. A process of claim 1, which is carried out at a pressure of $1 \cdot 10^5 - 2 \cdot 10^7$ pascal.

19. A process of claim 1, which is carried out in the temperature range from 0–300° C.

20. A process of claim 1, which is carried out in the temperature range from 20–200° C.

21. A process of claim 1, which is carried out as a batch process.

22. A process of claim 1, wherein the aromatic nitro compound comprises electrophilic substituents.

23. A process of claim 1, wherein the aromatic nitro compound is 4,4'-dinitrostilbenedisulfonic acid or a compound of formula II, III or IV.

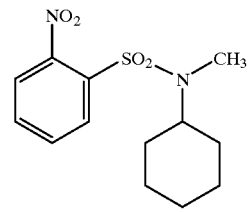
(II)

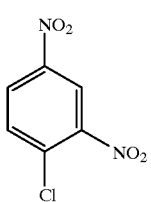
(III)

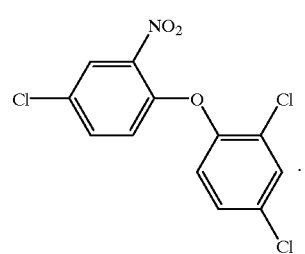
(IV)

* * * * *